United States Patent [19]

Meyer

[11] Patent Number: 5,012,820

[45] Date of Patent: May 7, 1991

[54] DEVICE FOR INVESTIGATION OF MUSCULAR CONTRACTION

[76] Inventor: Niels Meyer, Adalbertstrasse 7a, 6000 Frankfurt am Main, Fed. Rep. of Germany

[21] Appl. No.: 113,280

[22] PCT Filed: Dec. 10, 1986

[86] PCT No.: PCT/DE86/00504
§ 371 Date: Aug. 11, 1987
§ 102(e) Date: Aug. 11, 1987

[87] PCT Pub. No.: WO87/03466
PCT Pub. Date: Jun. 18, 1987

[30] Foreign Application Priority Data

Nov. 12, 1985 [DE] Fed. Rep. of Germany ....... 3543763

[51] Int. Cl.$^5$ .............................. A61B 5/10
[52] U.S. Cl. ..................... 128/782; 128/741
[58] Field of Search .................. 128/421, 423 W, 740, 128/741, 774, 782

[56] References Cited

U.S. PATENT DOCUMENTS

| | | | |
|---|---|---|---|
| 4,236,528 | 12/1980 | Stanec et al. | 128/741 |
| 4,571,750 | 2/1986 | Barry | 128/774 |
| 4,668,581 | 8/1987 | Moss | 128/741 |
| 4,724,842 | 2/1988 | Charters | 128/423 W |

*Primary Examiner*—Alan Cannon
*Assistant Examiner*—Randy Shay
*Attorney, Agent, or Firm*—Michael J. Striker

[57] ABSTRACT

The invention is directed to a device for the determination of the change in the mechanical magnitudes during muscular contraction and for the correlation with the change in the electrical magnitudes of nerve and muscle during muscular contraction. The body part with joint, which is to be investigated, is attached to a bolster (2) which rotates sagittally and is supported by means of axles (7, 8) on a line coinciding with the axis of rotation of the joint. An electromagnetically controlled functional coupling (10) and an electric motor (9) are connected to the axle (7) so as to be controllable, and horizontally extending flexure beams (27, 28), with stress measurement strips (29, 30), are fastened at the longitudinal sides of the electric motor (9). A potentiometer (11) and a torque measurement strip (31) are arranged on the axle (8). Electrodes (49, 50 and/or 51, 52) are arranged above the contracting muscle or its nerve and/or a stethoscope head (53), with a microphone (54) coupled thereto, is arranged above the muscle. Stress measurement strips (29, 30), potentiometer (11), electrodes (49, 50, 51, 52) and stethoscope/microphone (53, 54) are connected with an electric amplifier (40), and the latter is connected with a recording device (41). The muscle is excited by means of an electric stimulus current stimulator (39) and surface electrodes (42).

For the investigations of muscular contraction in smaller joints and muscles (e.g. in the hand), a rotatable frame is proposed as a further development, which consists of U-shaped structural component parts (69, 72), which are connected with one another and have shared axles (68), and is attached to the investigated body part (e.g. thumb) with the axles (68) on a horizontal line with the axis of articulation. The potentiometer (11) and the torque strips (31) are located on the axles (68). During the contraction of the muscle, the frame presses on the frame construction (80, 81, 82), which comprises a pressure plate (78), which is vertically movable in the latter, and a pressure spring (79), via a lever (75) with a double roller (77) which runs in defined cam guides (87).

29 Claims, 15 Drawing Sheets

DEVICE FOR INVESTIGATION OF MUSCULAR CONTRACTION

The invention is directed to a device for the determination of the change in the mechanical magnitudes during muscular contraction and for the correlation with the change in the electrical magnitudes of nerve and muscle during muscular contraction, preferably in the living human organism. In various scientific fields, particularly in medicine, biology and sports science, it is necessary, or at least useful, during investigation of the skeletal musculature to determine the change in the mechanical magnitudes of muscles and in the electrical magnitudes of muscles and the nerves assigned to them and to determine their correlation. For example, this is necessary for the observation of the course of rehabilitation programs and training programs in sports of the development of muscular diseases (e.g. muscular dystrophies). These determinations are likewise advisable for determining the dosage of medicines acting on the muscles or in anesthesia. In addition, it is relevant to medical and biological training in the fields of neurology, myomechanics, reflexes and electromyelography to obtain the most accurate possible values in the aforementioned sense with respect to the musculature during muscular contraction.

Specifically, in the field of medicine and in medical training, the determination of the change in the mechanical magnitudes and the determination of the reciprocal action with the change in the electrical magnitudes, which determinations were necessary per se, were not possible in the living organism, particularly the living human organism. Previously, only biopsies of the musculature of killed animals were usable, wherein the results of measurements with such test subjects were only to be related to the human organism by way of inference or by way of a corresponding utilization.

Moreover, various devices and methods for muscular testing and for the determination of movement processes or muscular strength in terms of magnitudes have become known. However, these methods have very considerable disadvantages. In particular, only some of the critical parameters for the required determinations have been determined, although scientifically correct results are to be obtained only by means of the determination and correlation of all parameters (total nerve potential, nerve conductive speed, total muscular potential, muscular vibrations, muscular strength, muscular path, and the various latency periods).

In addition, the known devices and methods already have the considerable disadvantage that they effect an insufficient fixing of the areas of the body, particularly the limbs, with respect to which the muscular contractions are to be investigated. This causes a falsification of the magnitudes which are determined subsequently, for example, by means of an incomplete detection of a part of the contraction and/or possibilities of deviation of the investigated limbs relative to the measuring device.

Finally, the known devices and methods have the disadvantages that the initial magnitudes and initial conditions for the investigations, particularly with respect to electric current stimulus intensity, intensity of the impulse during the use of a reflex hammer, and magnitude of the counterforce exerted on the respective muscle, cannot be established in such a way as to be unchangeable for the respective test or test series, and there is an additional source of error in the form of the inherent friction of the testing and measuring device. The proband the (i.e. individual actually being investigated) can also not be individually fitted in the testing device or measuring device in the known devices and methods, although this is indispensable in view of the existing differences in the bodily frame of individual persons.

The invention has the object of providing a device of the type mentioned in the beginning in which the change in the mechanical magnitudes, accompanied by the correlation with the change in the electrical magnitudes of the nerve and muscle during muscular contraction, can be reliably determined while eliminating sources of error and while avoiding the disadvantages of the known methods and/or devices.

This object is met, according to the invention, by means of the characteristic features noted in the characterizing part of patent claim 1. Advantageous constructions of the invention are noted in the subclaims.

In the following, the embodiment examples of the invention are described with the aid of the drawings.

Figure 1:
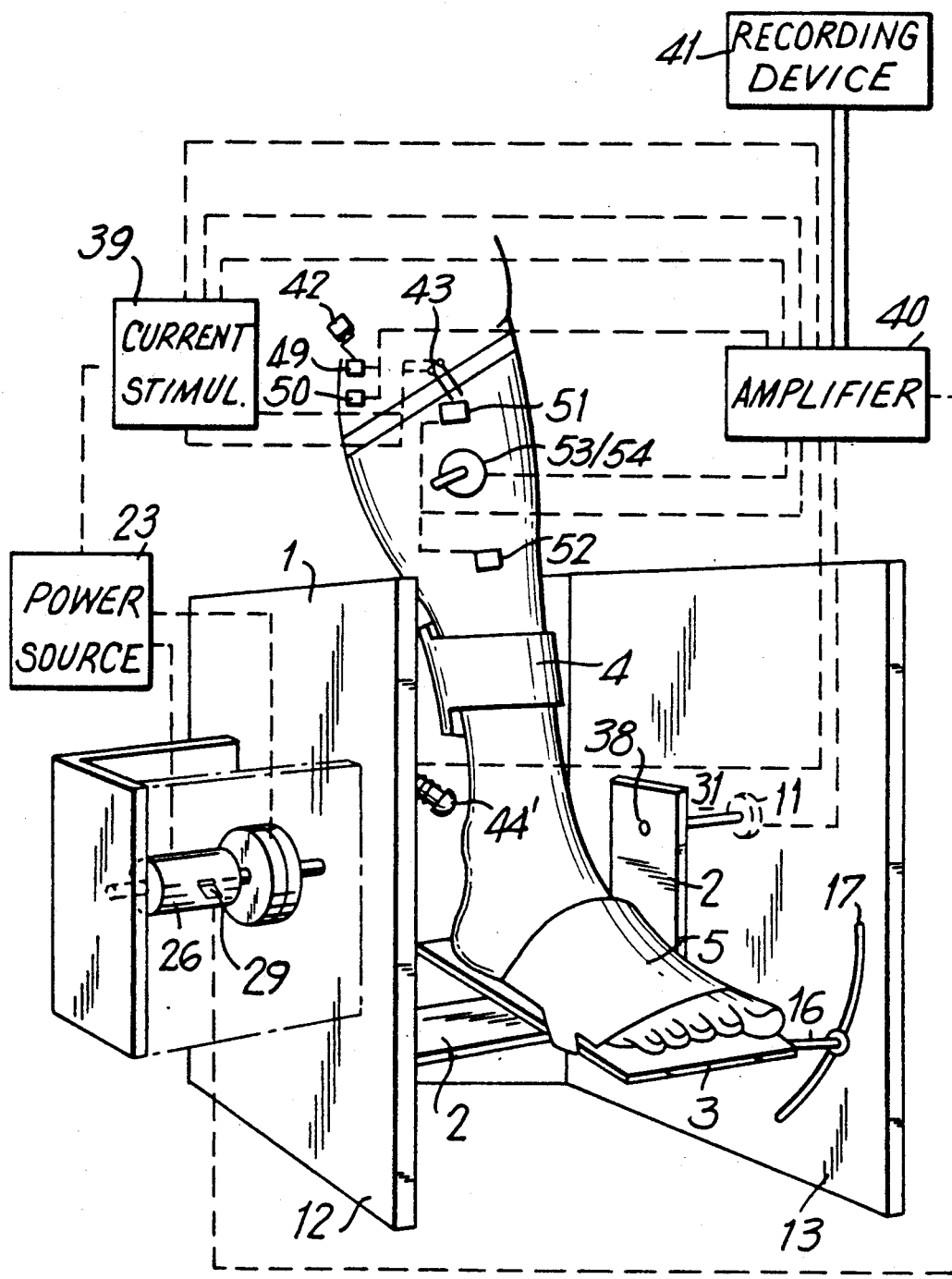
FIG. 1 shows an isometric drawing of the device, according to the invention, for the investigation of muscular contraction with fixed lower leg and foot.
Figure 2:
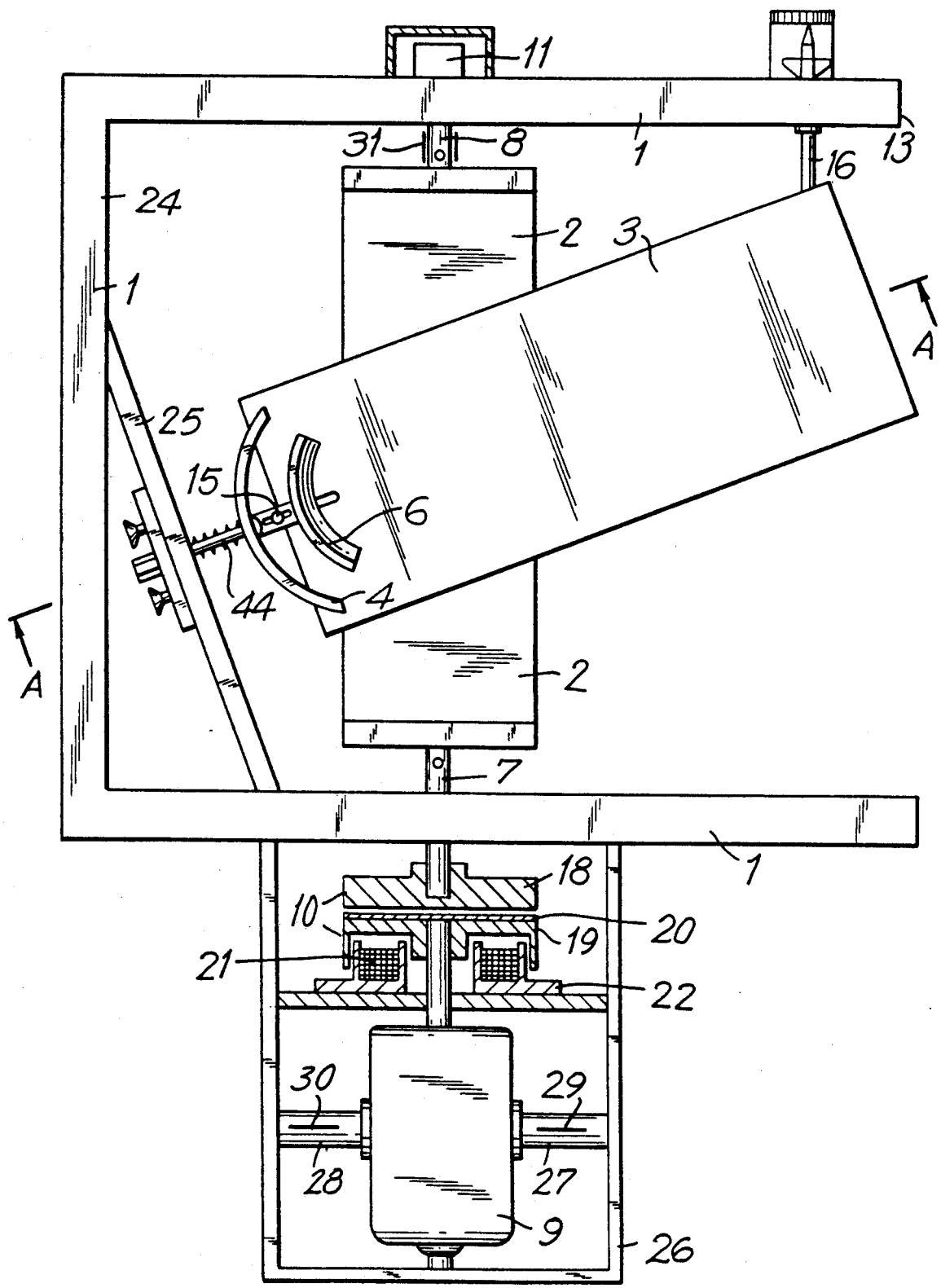
FIG. 2 shows a top view of the device according to FIG. 1, but prior to the fixing of the limb to be investigated on the right of the muscle area.

The device for the investigation of muscular contraction, according to the invention, consists of the housing 1, which is open on the front side, the top side and the lower side, the U-shaped rotating bolster 2, which is inserted in the housing and comprises a base plate 3 placed on top of the base of the bolster, the upper limb holder 4 and the lower limb holder 5—as well as the heel holder 6 in the embodiment example, according to FIGS. 1 and 2, which is shown—and the electric motor 9, including electric coupling 10, which electric motor 9 is connected with one vertical leg of the rotating bolster 2 via the axle 7, and the potentiometer 11, which is connected with the other vertical leg of the rotating bolster 2 via the axle 8. FIGS. 1 and 2 show the device, according to the invention, in its arrangement for the investigation of the contraction of the foot lifting muscle (musculus tibialis anterior), which, however, can also serve for the investigation of the calf musculature (lowering of the foot). The rotating bolster 2 is inserted in the housing 1 so as to be rotatable in the sagittal plane by means of the two axles 7 and 8, each of which is attached in the upper area of the two vertical legs of the rotating bolster 2 and guided, preferably with ball bearings, through the outer wall 12 and 13 of the housing 1, which outer wall 12 or 13 extends parallel to them. The base plate 3, for the placement of the foot, is attached to the base piece of the rotating bolster 2 so as to be vertically adjustable by means of the rotational adjustment 14 and in such a way that it can be changed with respect to its inclination by means of a spherical head. A heel holder 6 is provided at the rear end of the base plate 3 in an advantageous manner and is horizontally displaceable in the longitudinal direction of the base plate by means of a detachable fastening device, known per se, and fixes the heel of the respective proband.

As shown in FIG. 1, the lower limb holder 5 serves for additional fixing and prevention of unwanted horizontal and/or vertical movements of the foot. In an advantageous embodiment form, this consists of a cup of thermoflexible plastic which adapts to the respective form of the instep of the foot and is fastened at the base plate 3.

In a manner which is likewise not necessary to the invention, but which is advantageous, a stop support 16 is provided below the base plate 3 and attached so as to be fixed, but detachable and vertically adjustable, in a recess 17 in the outer wall 13 of the housing 1, which recess 17 extends in a curve-shaped manner, the respective desired lower end position of the base plate 3 and, accordingly, of the rotating bolster 2, at the same time, being refined by the support 16.

The electric coupling 10 and the electric motor 9, which is connected to the latter, are attached to the axle 7 at the outer side 12 of the housing 1. The electric coupling consists of the two disks 18 and 19, which adjoin one another, wherein at least the coupling disk 19 comprises a friction/brake lining 20. The force-locking connection of the coupling and the contact force of the disks 18 and 19 are effected by means of an electromagnet 21, 22, in a manner known per se, so as to be controllable, the electromagnet 21, 22 being fed by an electric current source 23. The coupling disk 19 is connected via the axle 7 with the electric motor 9 which is also fed by an electric current source 23, its speed being controllable.

At the opposite outer wall 13 of the housing 1, the potentiometer 11 is attached at the outside of the outer wall on the axle 8.

Figure 3:
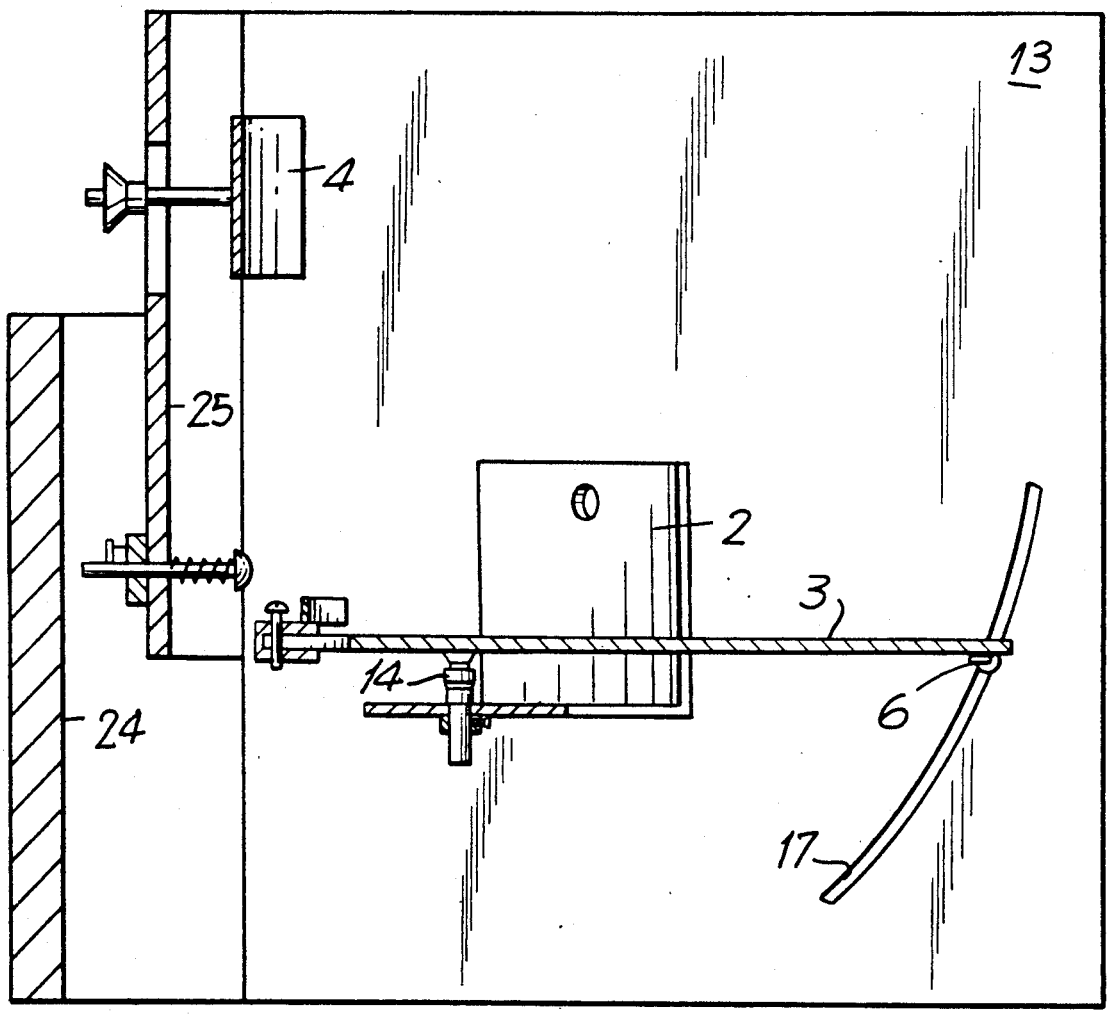
FIG. 3 shows a longitudinal section through the device according to FIG. 2 of section point A—A.

In order to fix the shank or the lower part of the leg of the proband in the device, the upper limb holder 4 is provided at the rear wall 24 of the housing 1 with the intermediary of a retaining wall 25, as can be seen in FIGS. 1 to 3; the limb holder 4 is adjustable vertically and/or horizontally by means of known adjusting screws in order to adapt to the shank of the respective proband and has a binding or half-shell for clamping the shank.

The electric motor 9 is not securely flanged on at the outer wall 12 of the housing 1 or at the housing 26, which encloses the electric coupling and electric motor. Rather, the axle 7 is guided through and is supported in the outer wall of the housing 26 in a ball bearing. As shown in FIG. 2, horizontally extending flexure beams 27, 28 are fastened to the housing 26 with stress measurement strips 29 at the two longitudinal sides of the electric motor 9. Instead of, or in addition to, these flexure beams 27, 28 with stress measurement strips 29, 30, a torque measurement strip 31 can also be attached on the axle 8 between the vertical leg of the rotating bolster 2 and the potentiometer 11.

Figure 4:
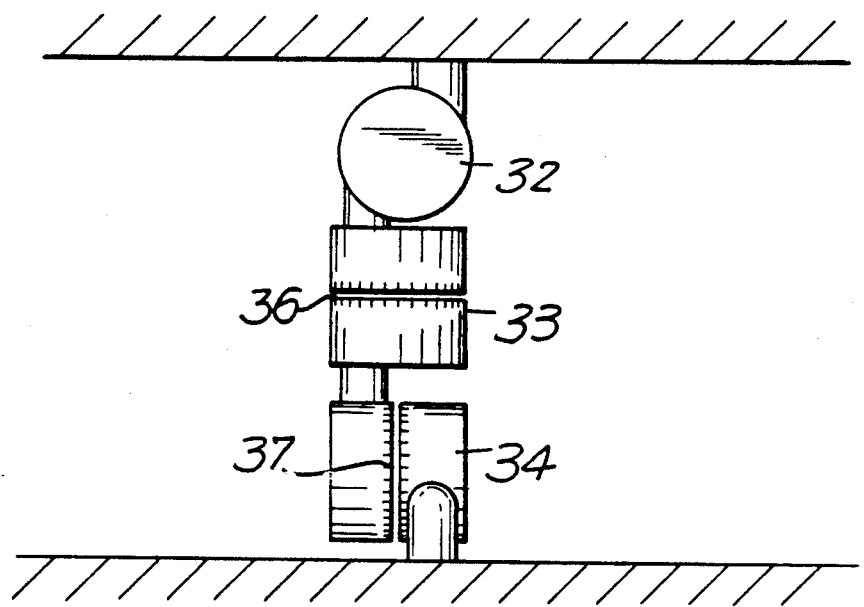
FIG. 4 shows on an enlarged scale a side view of the rotational adjustment between the base plate and the rotating bolster in the device of FIG. 3.
Figure 5:
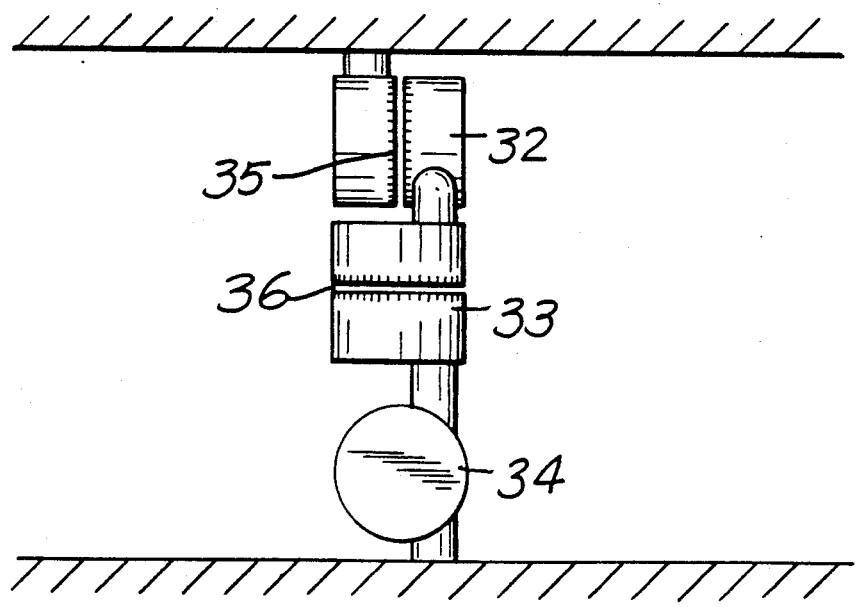
FIG. 5 shows an alternative construction of the rotational adjustment as in FIG. 4, but in a front view, as a detail.

As shown in FIGS. 3 to 5, the rotational adjustment 14 has a measurement scale for fixing or determining the distance between the base plate and the base piece of the rotating bolster 2. Three pairs of corresponding disks 32, 33, 34, which can be securely connected and detached again in each instance, are arranged vertically one above the other and are connected with one another via one of the disks in each instance, wherein the upper pair of disks 32 and the lower pair of disks 34 are arranged in the vertical direction so as to be offset relative to one another by 90°, and the middle pair of disks 33 are arranged horizontally. Scales 35, 36, 37 are attached at each of the three pairs of disks 32, 33, 34.

Feelers 38, which can be pulled out of the axle in the horizontal direction in a telescopic manner or pressed out by means of inserted springs, are set in at the respective inner ends of the axles 7 and 8, which ends penetrate the vertical legs of the rotating bolster 2. These feelers are advanced to the highest projections of the ankles, as axis of rotation of the upper ankle joint of the leg, during the preparation of the investigations with the device according to the invention. After this, the base plate 3 is fixed by means of the rotational adjustment 14 and the adjustment of the support 16 in such a way that the axis of rotation of the ankle joint lies in an imaginary horizontal line with the axles 7 and 8.

After fixing, the feelers 38 are guided back into the axles 7 and 8 again.

As shown only schematically in FIG. 1, a stimulus current stimulator 39, an amplifier 40, and a charting or recording device 41 are attached at the housing 1 of the device according to the invention, in addition, the stimulus current stimulator 39 being fed via the electric current source 23. The surface electrodes 42, or the needle electrodes 43, as desired, which electrodes 42 or 43 excite the muscle, are connected to the stimulus current stimulator 39.

A reflex hammer 44, which is attached to the retaining wall 25 in the area of the Achilles tendon in the shown embodiment example, according to FIGS. 2 and 3, can be provided for triggering the muscular contraction as an alternative to the surface electrodes 42 and the needle electrodes 43, as shown in FIGS. 2 and 3. It is triggered by means of tensioning and relaxing a spring 45 with a catch 46. Located in the hammer head 44' is a piezoelectric element 48 which transmits an electric impulse of varying intensity depending on the intensity of the blow of the reflex hammer 44 to the tendon or muscle.

According to FIG. 1, in order to obtain measurement values during the contraction of the muscle, the two electrodes 49 and 50 for measuring the total potential and conductive speed of the nerves are attached above the nerve of the contracted muscle, and the additional electrodes 51 and 52 for measuring the electric potential fluctuations (EMG) are attached above the contracted muscle, alternately or cumulatively. These electrodes are connected with the amplifier 40. In addition, the stethoscope head 53, including a microphone 54 which is coupled thereto, is attached above the muscle in order to measure the muscular vibration, the microphone 54 likewise being connected with the amplifier 40.

There is also a connection between the potentiometer 11 and the amplifier 40 and a connection between the stimulus current stimulator 39 and the amplifier 40. Insofar as the reflex hammer 44 is attached, its piezoelectric element 48 is also connected with the amplifier. Finally, there is a connection between the electric motor 9 and the amplifier 40 in order to take into account its respective power potential.

The impulses of the aforementioned measuring points or data transmitters, which impulses are amplified in the amplifier 40, are recorded in the connected recording device 41 in the course of the test.

The following test sequence results by means of the described device: After fixing the foot and the shank of the proband in the device, according to the invention, by means of the upper limb holder 4 and on the base plate 3, and after fixing the support 16, the surface electrodes 42 and/or the needle electrodes 43, on the one hand, and the electrodes 49, 50 and/or 51/52, as well as the stethoscope head 53, are applied. Next, the electric motor 9 is brought to a constant speed with a predetermined current by means of the electric current source 23. The electric motor 9 drives the disk 19 of the electric coupling 10 which is securely connected with it. A connection of the coupling disks 18 and 19 of greater or lesser strength is produced by means of pressing, preferably with residual slippage, by means of exciting the electromagnets 21, 22 with a predetermined current via the current source 23. In the shown embodiment example, the rotational force acts in the clockwise direction. Via the axle 7 and the vertical leg of the rotating bolster 2 connected with it, the latter, with the base plate and the foot of the proband, is pushed forward in a downward direction in the toe area until the base plate 3 abuts against the stop support 16. The muscle is then excited by means of the current source 23, the stimulus current stimulator 39 and the electrodes 42 and/or 43, or by means of the reflex hammer 44, and is accordingly made to contract. During a muscular contractive force which is greater than the frictional force between the coupling disks 18 and 19, the foot together with the rotating bolster 2 moves upward in the counterclockwise direction around the axis of rotation of the ankle joint, and the axles 7 and 8, which extend along with it on an imaginary line. The potentiometer 11 on the axle 8 measures the position of the axle in relation to the entire scope of movement during this rotating movement and the rotation of the axle during the contraction and transmits the measured value to the recording device 41 via the amplifier 40. The values measured by the electrodes 49, 50 and/or 51, 52 and by the stethoscope head 53 are directed to the recording device 41 via the amplifier 40 at the same time.

Figure 6:
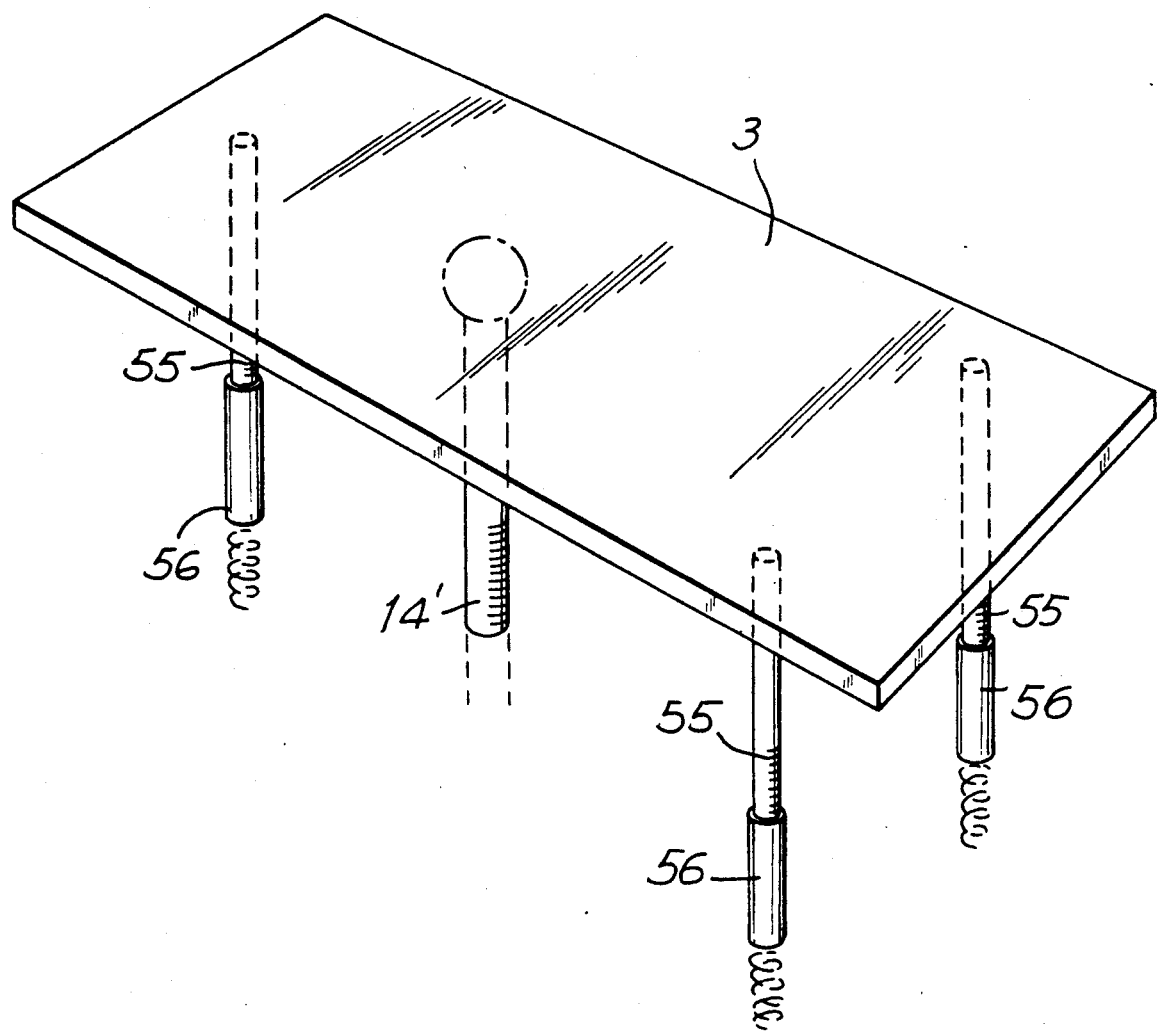
FIG. 6 shows another alternative of the rotational adjustment between the base plate and the rotating bolster of the device as a detail.
Figure 7:
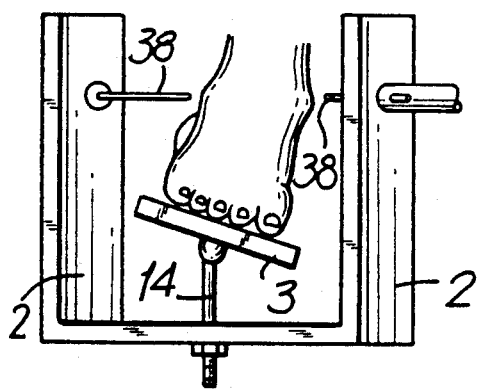
FIG. 7 shows the rotating bolster with base plate and feelers attached at the foot for the purpose of fixing, as a detail.
Figure 8:
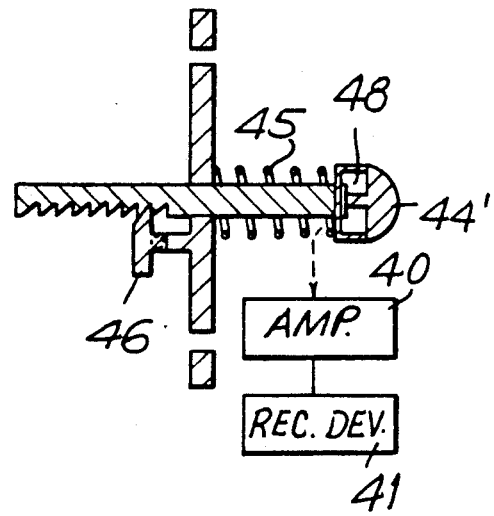
FIG. 8 shows the reflex hammer of the device as a detail from FIG. 3.
Figure 9:
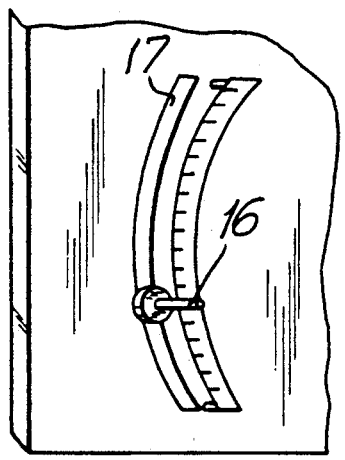
FIG. 9 shows the support for the base plate together with the guide in the outer wall of the device, as a detail from FIGS. 1 and 2.

A rotational adjustment 14' comprising a spherical head is provided in FIG. 6 as an alternative to the rotational adjustment 14 with the measurement scale. In addition, one or more measuring rods 55, which are provided with scales, extend perpendicularly relative to the plane of the base plate 3 and comprise resilient sleeves 56, are attached at the underside of the base plate 3 and extend until the base piece of the rotating bolster 2 and indicate the distances between the base plate 3 and the base piece of the rotating bolster 2 after the lower leg and foot, or other body part of the proband, is fixed with the rotational adjustment 14'.

Figure 10:
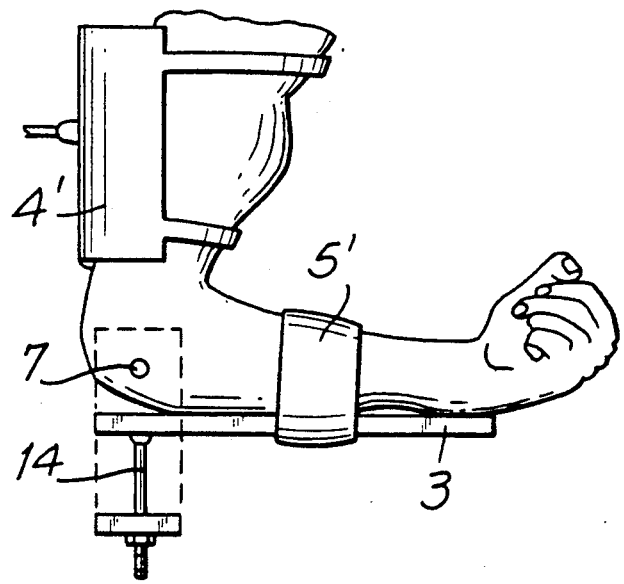
FIG. 10 shows the construction of the device, according to the invention, for the investigation of the contraction of the arm musculature as a detail.
Figure 11:
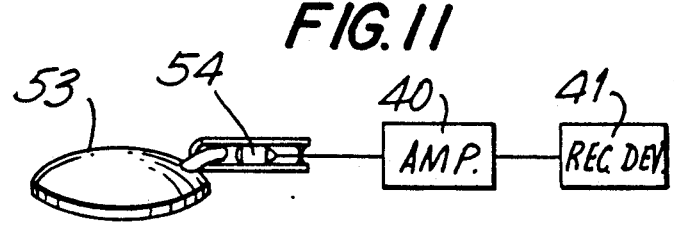
FIG. 11 shows the stethoscope head with microphone for measuring the muscular vibration, as a detail from FIG. 1.

FIG. 10 shows the device, according to the invention, in its arrangement for the investigation of the contraction of the upper arm muscle. As can be seen from this, it is only necessary to adapt the upper limb holder 4' and the lower limb holder 5' to the differing anatomy of the arm with the construction of the device remaining unchanged in other respects.

Figure 12:
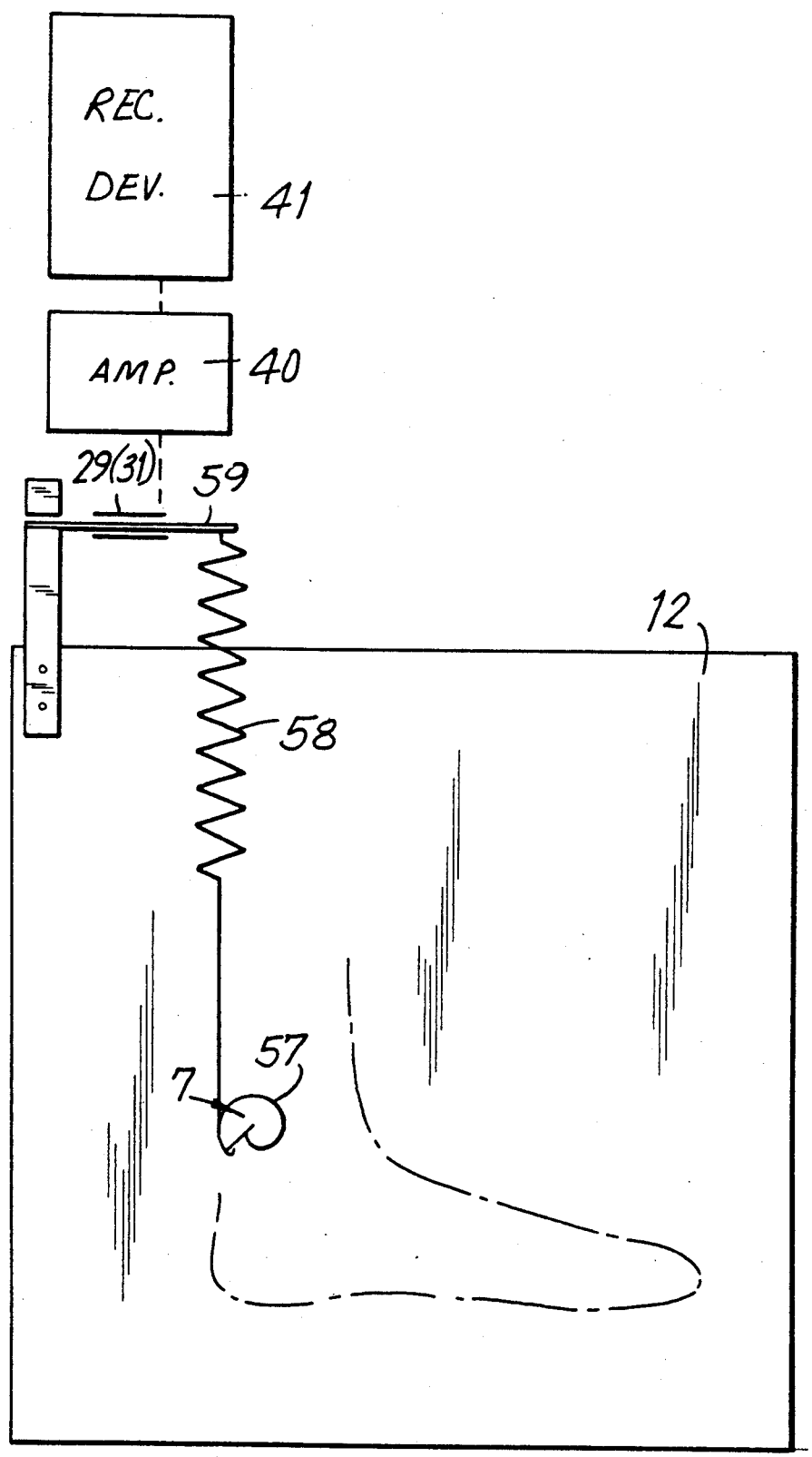
FIG. 12 shows another embodiment example of the device, according to the invention, with tension spring as counterforce and helical roller in a schematic presentation.

Another embodiment form of the device, according to the invention, is shown in FIG. 12. Instead of the motor 9 and the coupling 10, the axle 7 is attached at the outside of the outer wall 12 with a helical roller 57 and a connected vertically arranged spiral tension spring 58, which is attached, in turn, to a horizontally extending flexure beam 59 attached at the outer wall 12. In cross section, the helical roller preferably has the shape of a curve according to the following formula:

$$r(\phi) = r_o \left(1 + 2\frac{r_o}{x_o} \phi \right)^{-\frac{1}{2}},$$

with the tracking error angle $\psi$ $$\cos\psi = \left(1 + 2\frac{r_o \cdot \phi}{x_o}\right) \cdot \left[\left(1 + 2\frac{r_o \cdot \phi}{x_o}\right)^2 + \left(\frac{r_o}{x_o}\right)^2\right]^{-\frac{1}{2}}$$

wherein $\theta$ is the angle of rotation, $r_o$ is the initial radius, $r(\theta)$ is the radius after the rotation of the roller by a determined angular distance via the axle 7, and $x_o$ is the initial pretensioning of the spiral tension spring 58. By means of the helical roller 57, which is designed in this way, the extension of the spiral tension spring 58, which is brought about by means of the rotation of the rotating bolster 2 and the axle 7 during the contraction of the muscle, and the tensile force, which increases thereby, are compensated, and a constant torque is achieved.

The spiral tension spring 58, with a tensile force selected as needed, can be exchanged with others of the same length, but with greater or lesser tensile force. In this case, as well, the torque remains constant due to the helical roller 57. In this embodiment form, the spiral tension spring 58, instead of the combination of electric motor and electric coupling, acts as a counterforce against the force of the contracted muscle. The force which acts on the flexure beam 59 via the axle 7, the roller 57 and the spiral tension spring 58 during the muscular contraction is amplified by means of an amplifier 40, as in the embodiment example described above, and is transmitted to the recording device 41. The connection between the lower end of the spiral tension spring 58 and the roller 57 is produced by means of a material which is stable with respect to length, such as polyamide wire, for example. In a further development of this embodiment form, it is also possible to arrange a plurality of spiral tension springs 58 having various tensile forces and to connect them with a change-gear unit in such a way that contraction tests, which are spaced at brief intervals, can be carried out in a test series with differing counter-forces of the spiral tension springs.

Figure 13:
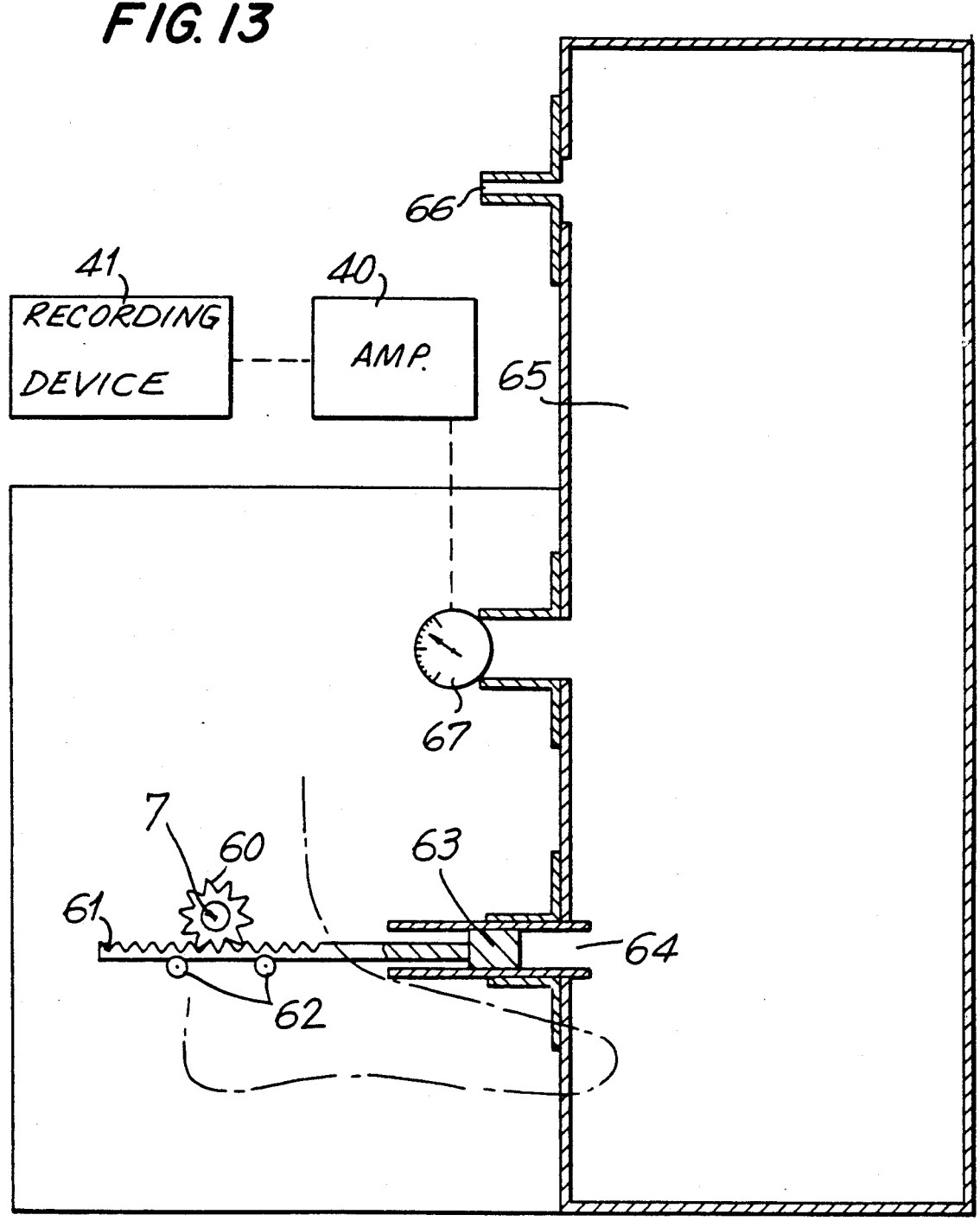
FIG. 13 shows another embodiment form of the device, according to the invention, with container, which is filled with compressed air, as counterforce to the muscular contraction.

In FIG. 13, as another embodiment form of the device, according to the invention, a toothed wheel 60 is attached at the axle 7 on the outside of the outer wall 12, instead of the electric motor and electric coupling 9 and 10, the toothed wheel 60 engages in an adapted toothed rail 61 which is horizontally displaceable in both directions on two or more rollers 62. At one of its ends this toothed rail has a piston 63 which is displaceable in an adapted cylindrical output 64 of a compressed air tank 65. This compressed air tank can be put under pressure, which can be selected as desired, via the feed 66, the pressure being measured by means of the manometer 67 and transmitted to and recorded by the recording device 41 as a measurement value via the amplifier 40. Because of the relatively large volume of the compressed air tank 65, the internal pressure, which prevails in the latter and acts as a counterforce against the pressure occurring during the muscular contraction via the axle 7, the toothed wheel 60, the toothed rail 61 and the piston 63, remains practically constant. The rest of the construction and arrangement of the device is not changed relative to that described in the beginning.

Figure 14:
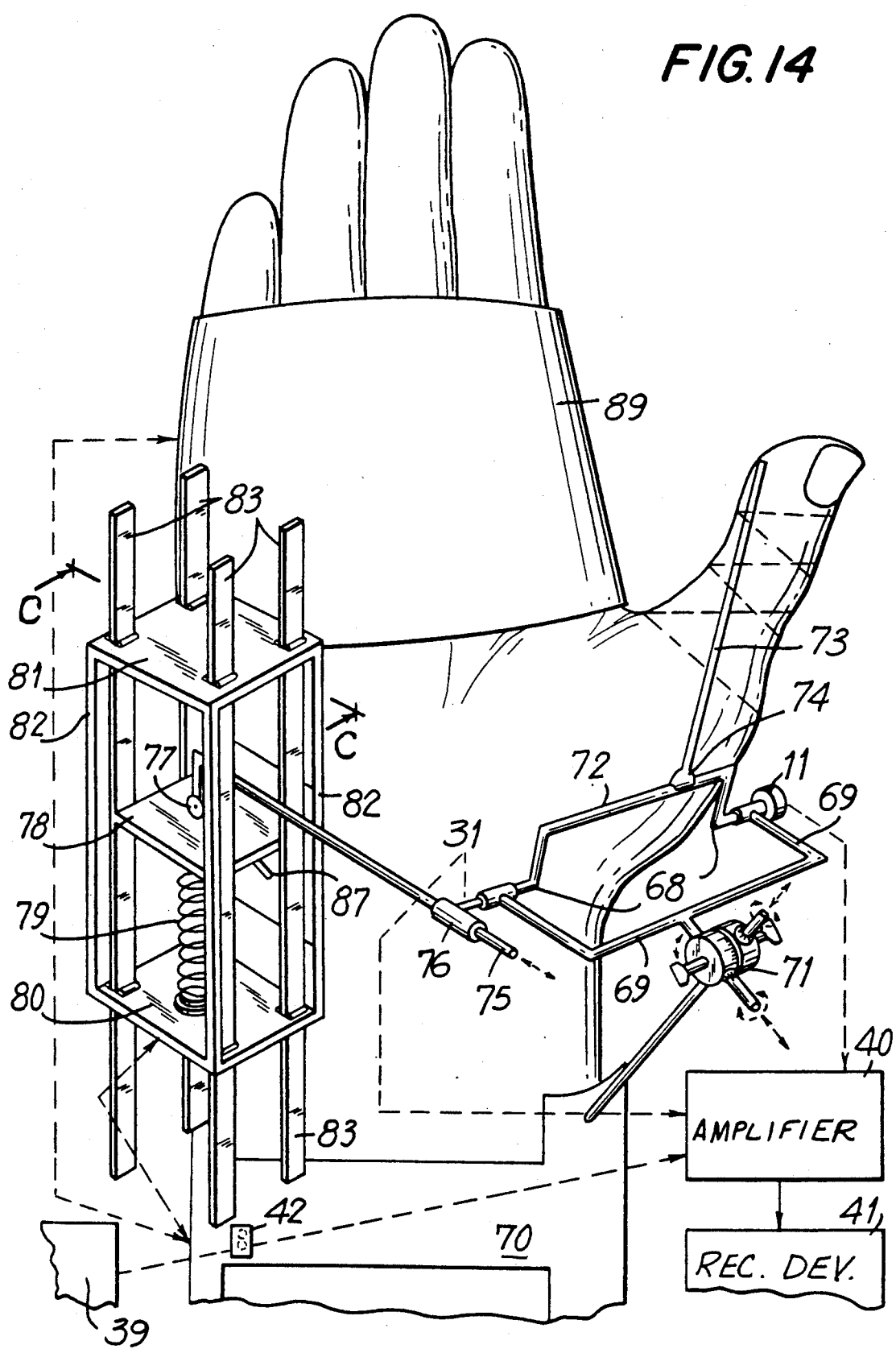
FIG. 14 shows the adapted device for the investigation of the muscular contraction of the thumb muscle as another embodiment form.
Figure 15:
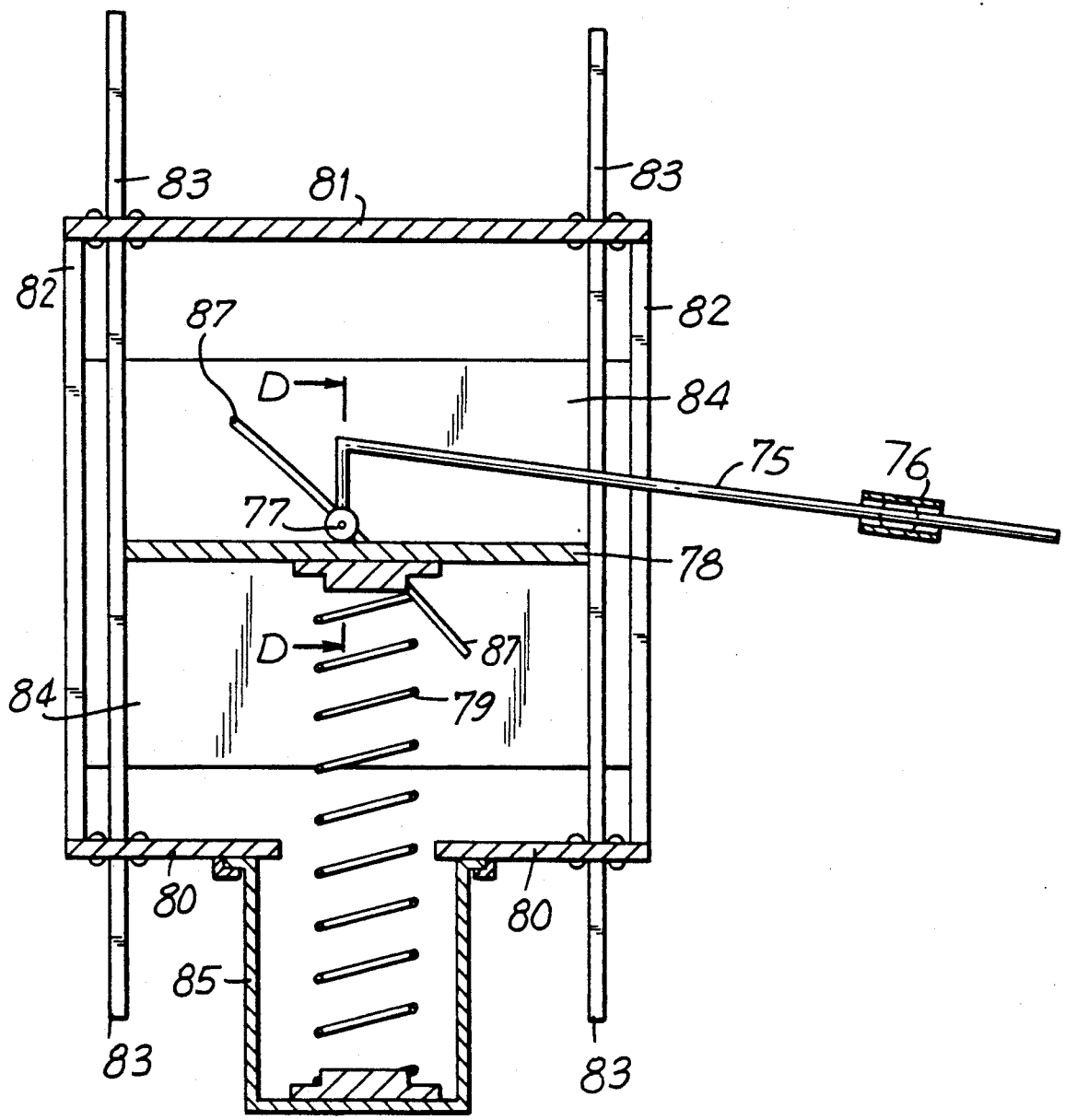
FIG. 15 shows a section at point C—C as a detail from FIG. 14.
Figure 16:
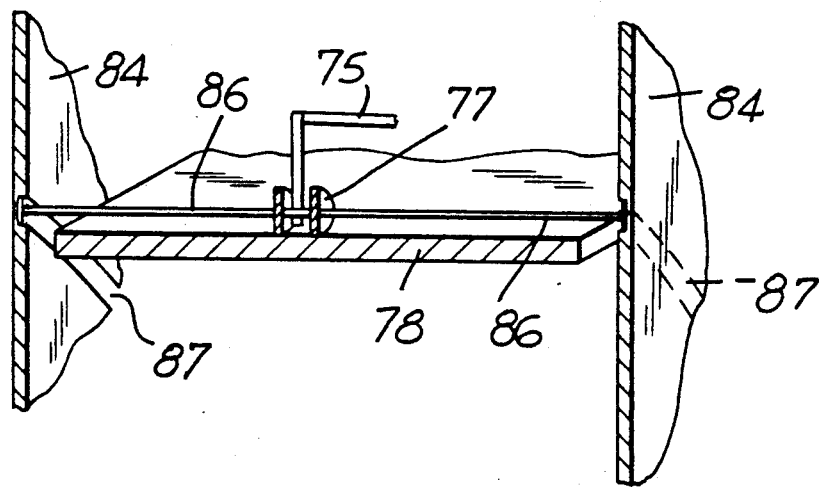
FIG. 16 shows a section at point D—D as another detail.

In FIGS. 14 to 16, as another embodiment form, the device, according to the invention, is shown as adapted to the investigation of muscular contraction in smaller joints and muscles by way of the example of the muscle which draws the thumb in the direction of the fingers. The axles 68, which extend on either side of the thumb, lie on the imaginary line of the axis of articulation of the articulatio carpometacarpea pollicis joint, and are connected by means of the U-shaped structural component part 72, are supported at the end points of a structural component part 69 which is likewise U-shaped and is fastened at the lower arm holder 70 by means of the adjusting device 71 which comprises a measurement scale, can be pulled out and is rotatable in a three-dimensional manner. A strip 73, which serves as a limb holder like the limb holder 5 described above and is placed so as to be flush with the surface of the thumb in the rest position, is attached at the U-shaped structural component part 72 by means of a fastenable joint 74. The thumb is fixed at the strip 73, for example, by means of quick-hardening rigid bandages. A lever 75 is attached horizontally and at a right angle to the axle 68, it is supported in a guide 76 and is longitudinally displaceable therein. The lever 75 is bent down at the opposite end; it carries a movable double roller 77 at its outermost end. The lever 75 presses on the center plate 78 via this double roller 77 during the contraction of the thumb muscle, the center plate 78 receives the counterforce to the muscular force by means of the pressure spring 79. The pressure spring 79 is securely connected with the base plate 80 as a lower part of a frame construction which consists of the base plate 80, the cover plate 81 and the four outer struts 82. Four inner struts 83, which are guided in each instance between rollers attached in the base plate 80 and the cover plate 81, extend through the base plate 80 and the cover plate 81. The struts 83 are fixedly connected with the center plate 78. When the thumb moves by means of contraction of the muscle the axles 68 rotate, wherein the lever 75 is moved downward against the spring force of the pressure spring 79. In order to compensate for the spring force which changes during the compression of the pressure spring 79, the double roller 77 moves along its rotational axis, which is lengthened toward both sides, into two elongated holes 87. The latter are contained in two side walls 84 located opposite one another. One of these side walls 84, with elongated hole 87, is visible in FIG. 15. The pressure spring 79 can be exchanged for springs of the same length, but with different spring constants, in that it is detached with its supporting cylinder 85 with a bayonet catch. If the lever 75 moves downward or upward, the double roller 77 is guided into the elongated holes 83 by means of its axial elongations 86, which engage in the elongated holes 83. In so doing, the lever 75 is displaced in its guide 76 and accordingly changes the operative lever length. The elongated holes 83 describe a mathematically determined curve which advantageously extends according to the formula:

$$r(\phi) = \frac{-Y_o + \sqrt{Y_o^2 + 2\frac{M_o}{k}\phi}}{\sin\phi}$$

In this case, r ($\theta$)=operative lever length as connection of the point of rotation in the guide 76 to the starting point of the double roller 77 during rotation around the angle consisting of the horizontal lines; r ($\theta=0$)=r in the horizontal position; $Y_o$=compression of the spring at r ($\theta=0$); $M_o$=constant torque along the entire area; k=spring constant.

Figure 17:
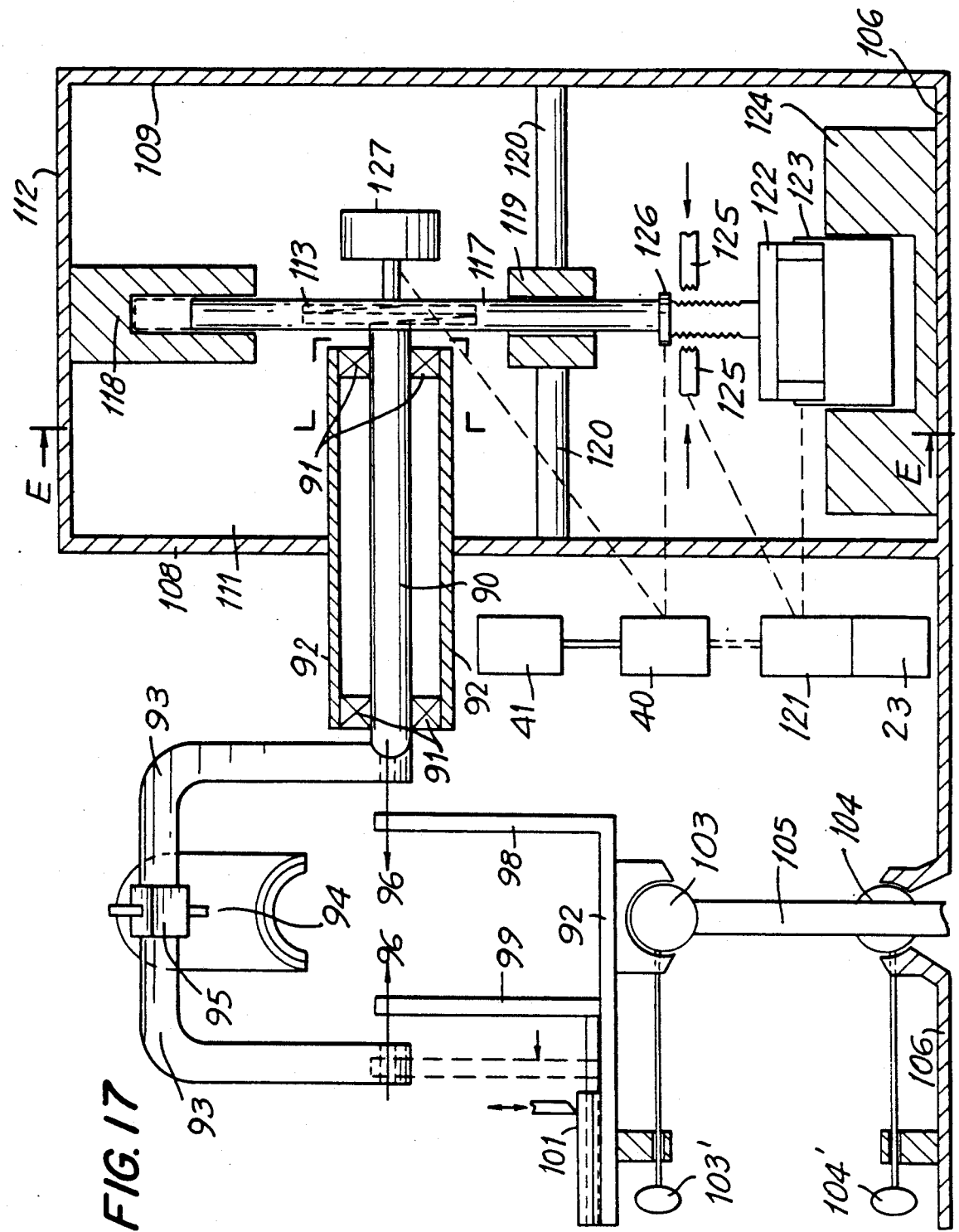
FIG. 17 shows another embodiment form for the investigation of the muscular contraction of the thumb muscle in a front view.
Figure 18:
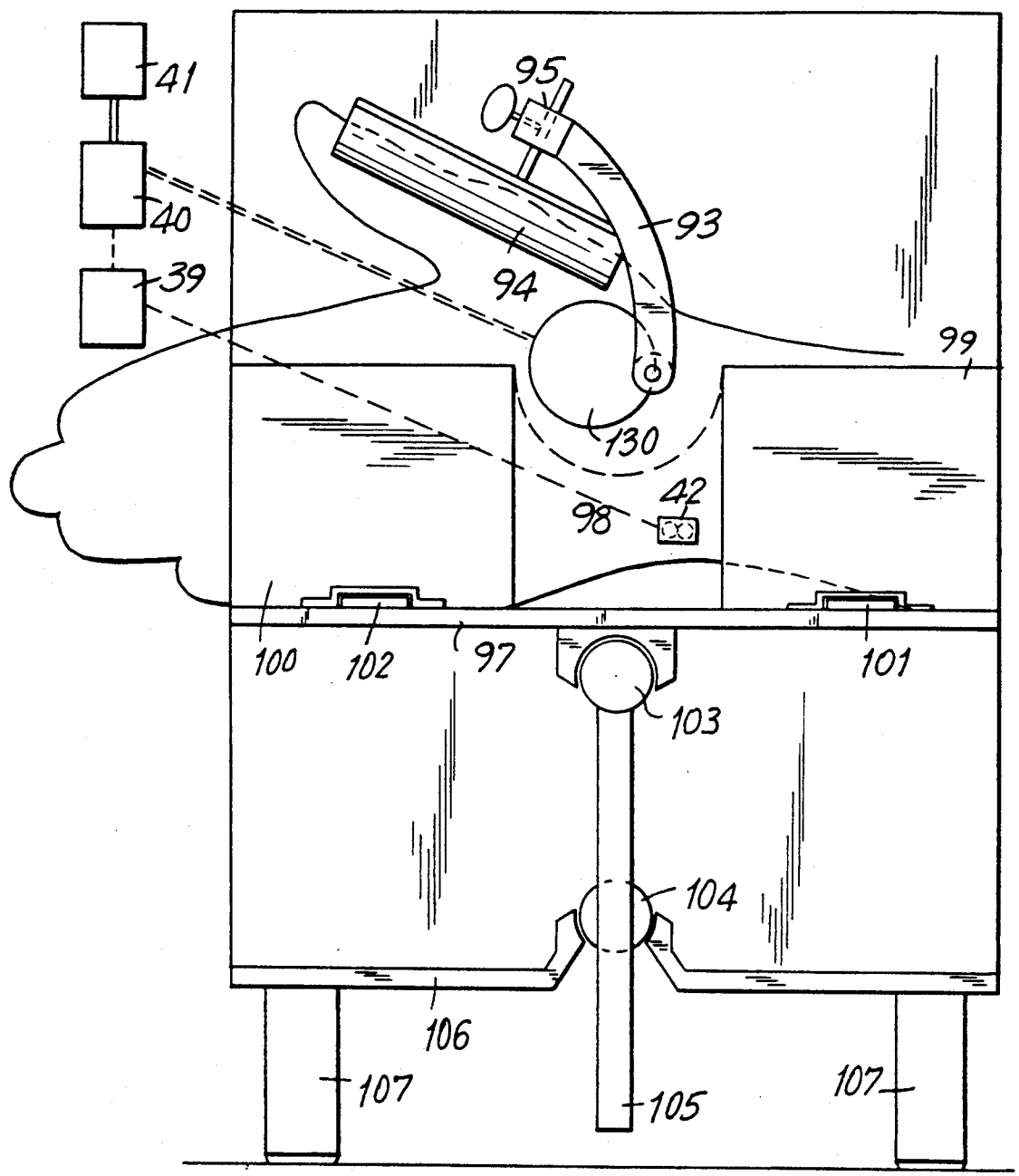
FIG. 18 shows a side view of the hand holder and thumb cup, as a detail from FIG. 17, with inserted and fixed hand.
Figure 19:
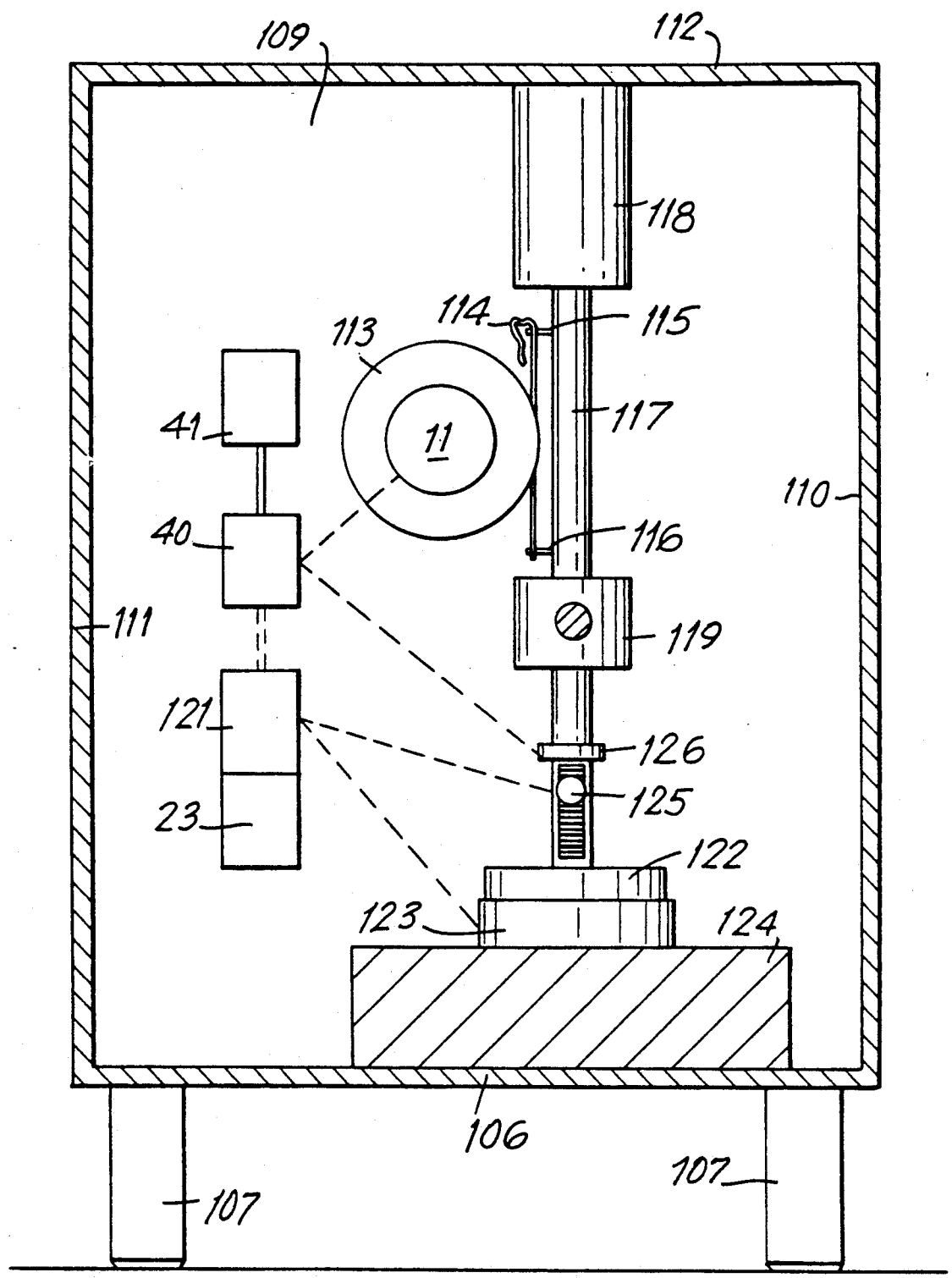
FIG. 19 shows section point E—E as another detail of FIG. 17.

In FIGS. 17 to 19, in a further development of the embodiment form of the device, according to the invention, for the investigation of muscular contraction in smaller joints and muscles, particularly that of the muscle which pulls the thumb in the direction of the fingers, the thumb, as seen in FIG. 18, is inserted in the thumb cup 94 and fixed on it, for example, by means of quick-hardening rigid bandages. The thumb cup 94 is fixedly connected with a fixing joint, known per se, via a holder 95, and the stirrup 93 is fixedly connected with the axle 90. This axle 90 is connected with a translating gear wheel 113 via two ball bearings 91, which are arranged so as to be parallel within the bearing support pipe 92, the translating gear wheel 113 being likewise arranged so as to be parallel to the stirrup 93, and carries the potentiometer 11 at its end opposite the stirrup 93. The hand holder 97, 98, 99, 100, which is arranged below the thumb cup 94 and the stirrup 93, is provided for the adapted support and fixation of the hand of the proband when carrying out the tests. The hand holder consists of the base 97, on which the edge of the hand is placed, the outer wall 98, which is attached at the base 97 at a right angle and is intended for the placement of the upper side of the hand, and the two outer walls 99 and 100 for the placement of the inside of the hand, which outer walls 99 and 100 are likewise arranged at a right angle to the base 97, but are displaceable in the direction of the outer wall 98 along lockable rail guides 101 and 102. The hand holder 97, 98, 99, 100 is connected with the graduated support bar 105 by means of a support which is attached at the base 97 and comprises a graduated and fixable ball joint 103, 103', the support bar 105, in turn, being inserted in the base plate 106 of the device for the investigation of muscular contraction by means of the graduated fixable ball joint 104, 104'. The axle 90, with the bearing support pipe 92, is guided through the housing wall 108, which is rigidly arranged on the base plate 106 at a right angle to the latter, wherein the bearing support pipe 92 is in turn rigidly connected with the housing wall 108. In order to prepare for the investigation, the hand of the proband is inserted in the hand holder 97, 98, 99, 100 and the axis of articulation (axis of rotation of the articulatio carpometacarpea pollicis joint) is made to overlap with the axle 90 in an (imaginary) line by means of the ball joints 103, 104, displacement of the support bar 105 in the vertical direction via the ball joint 104, displacement of the outer walls 99 and 100 via the rail guides 101 and 102, and the measuring rods 96 at the axle 90. The thumb is then fixed in the thumb cup 94.

The translating gear wheel 113, which is attached on the axle 90 at the output side of the bearing support pipe 92 opposite the stirrup 93, cooperates with a rod 117, which is arranged at a right angle relative to the axle 90, but is not connected with the latter so as to be fixed, and which is movable in linear guides 118 and 119, 120 in its longitudinal direction so as to be as free as possible from friction. As shown in FIG. 19, this rod 117 has two cord or wire holders 115 and 116 in its area assigned to the translating gear wheel, with a tensioning device at least one of the holders, in which a cord (wire) 114, which is inserted in the thread of the translating gear wheel 113, is fastened by both ends. As can be seen in FIG. 17, one end of the rod 117 projects into the linear guide 118 so as to be movable in the longitudinal direction. An electric winding/coil 123, with a coil holder 122, is rigidly attached at its other end downstream of the linear guide 119, 120, the winding/coil 123 is inserted in, or penetrates, respectively, a magnet core 124, but is movable therein in the longitudinal direction of the rod 117 along with the latter. The electric coil is fed via the electric current source 23 and a current regulator 121 so as to be controllable, so that the rod 117 is pulled in or pressed out in its longitudinal direction in the magnet core 124 according to the differing intensities of the magnetic field which is built up.

When the investigated muscle is excited in the manner described in the beginning, likewise via the current source 23 and the stimulus current stimulator 39, and accordingly made to contract, it effects a rotational movement of the axle 90, and accordingly of the translating gear wheel 113 via the thumb cup 94 and the stirrup 93. This rotational movement is transformed into a longitudinal movement of the rod 117 by means of the cooperation of the translating gear wheel 113, the cord/wire 114 and the rod 117. By means of the described solenoid coil 122, 123, 124 and the current regulator 121, a force is exerted during the investigation which is directed against the force transmitted by the investigated muscle to the rod 117 and whose characteristic curve can be determined and controlled.

The forces acting on the rod 117 are recorded by means of a tension/compression recorder 126, preferably by means of a piezoelectric crystal or capacitor. The information concerning the rotation of the axle 90 effected by the contracting muscle is recorded via the potentiometer 11 as in the embodiment example according to FIGS. 1 and 14.

The impulses recorded by the tension/compression recorder 126 and by the potentiometer 11 are, in turn, amplified in the amplifier 40, as in the embodiment examples described in the beginning, and recorded in the connected recording device 41 together with the other described parameters.

For tests with purely isometric contraction, a fixing-/locking 125 of the rod 117 is provided, in a manner known per se, in order to adjust it securely in various initial positions; it is preferably constructed as a coil-magnet core switch and is likewise adjustable by means of the current source 23 and the current regulator 121. The rod 117, with the linear guides 118, 119, 120 and the electric solenoids 122, 123, 124, is advisably arranged in the test apparatus, as shown in FIGS. 17 to 19, in such a way that the magnet core is attached at the same base plate 106 as the hand holder 97-100 with support bar 105, and the linear guide 118 is securely connected with a cover plate 112, which cover plate 112 leads in the same plane as the base plate 106 and is securely connected with the wall 108 at a right angle. In a manner which is not necessary to the invention, but is advisable, the remaining open sides can be provided with the walls 109, 110 and 111 and an enclosed housing is accordingly formed.

Figure 20:
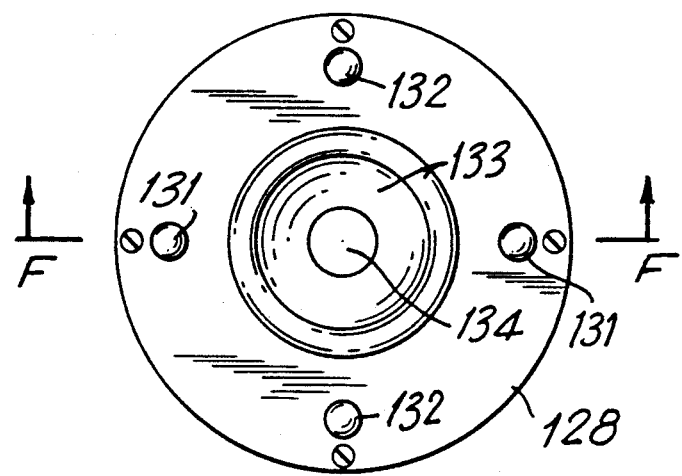
FIG. 20 shows the electrodes for the electromyograph, which electrodes are comprised in a structural component part, and the sound projector of the stethoscope head with a microphone connected downstream, in a view from below.
Figure 21:
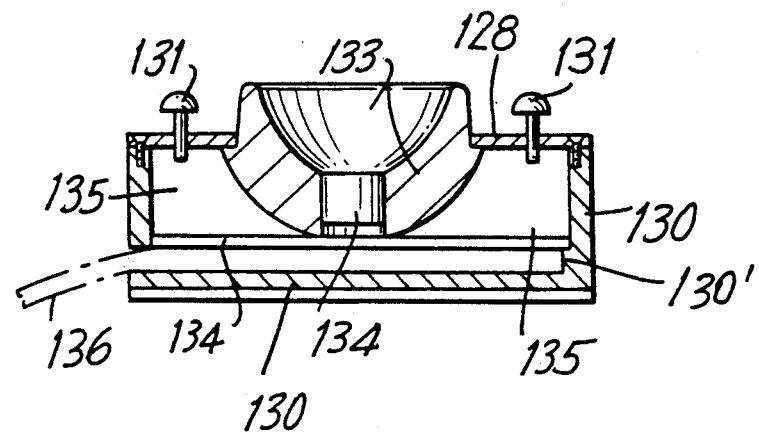
FIG. 21 shows the structural component part, according to FIG. 20, as a sectional drawing in a side view at section point F—F.

Finally, FIGS. 20 and 21 show an advantageous modification of the described electrodes 51 and 52 for measuring the electric potential fluctuations (EMG) and the stethoscope head 53 comprising a microphone 54 which is coupled thereto. The sound projector 133 corresponding to the stethoscope head 53 is inserted in a housing 130 with an open cover 128. The microphone 134 corresponding to the microphone 54 is connected downstream of the sound projector 133. Two differential electrodes 131 and two ground electrodes 132 of the electromyograph, which correspond to the electrodes 51 and 52, are likewise fastened in the cover 128 outside the passage of the sound projector. The electrodes 131, 132 and the microphone 134 are, as described, connected with the amplifier 40 and with the recording device 41 via the latter. However, it is also possible to arrange an amplifier, which corresponds to the amplifier 40, directly in the free interior space 135 of the housing 130 in order to amplify the impulses issuing from the electrodes 131, 132 and from the microphone 134, the amplifier being connected with the recording device 41. The structural component part described above is placed above the contracting muscle in a corresponding manner, as in the arrangement described in the beginning. Moreover, it can also be used over the heart muscle outside of the device, according to the invention, for the investigation of muscular contraction in order to simultaneously record the electrocardiogram and heart sound.

The device, according to the invention, offers the following advantages over the known devices and methods:

For the first time, it enables the detection of all decisive parameters for the determination of the change in mechanical magnitudes during muscular contraction and the correlation with the change in the electrical magnitudes of the nerve and muscle during muscular contraction.

The investigation of the musculature of humans and also animals is possible with living subjects and with an intact interrelationship of functions with a correlative analysis of the interrelationship. In particular, one need not make statements concerning human musculature, as was previously done, only through the transference of results from investigations on animals. In teaching, the biopsy of the musculature of killed animals, which was all that was usable previously, can be dispensed with, and the physiological interrelationship of the musculature can be taken as a topic in scientific training and observed in one's own body.

In addition, the device, according to the invention, enables the investigation of the musculature in virtually all skeletal muscular fibers, skeletal muscles and skeletal muscle groups; the described device and the principle of measurement on which it is based are continuously identical. It is only necessary to adapt the fixing devices to the respective area of the body under investigation. Because of the scientific reliability which is achieved, the results achieved with the device for the skeletal musculature, according to the invention, can also be transferred to the heart musculature and diaphragm musculature, for example, which is of particular importance for pharmacological research and anesthesia.

The device makes it possible to bring the excitation of the muscle to a defined magnitude as the starting point for all subsequent measurements. The stimulus for the excitation of the muscle is carried out supramaximally so that external influences which falsify the results of the investigation are eliminated. A maximal contraction of the muscle can also be triggered and can be measured and determined with the device in the sense indicated in the beginning.

The device, according to the invention, enables an accurate fixing which is adapted to the respective test subject and, particularly, allows the axis of rotation of the rotating bolster to be made to overlap with the axis of rotation of the investigated body part (e.g. with the axis of rotation of the upper ankle joint) as a decisive precondition for accurate investigation results. By means of accurately fixing the investigated body part, the forces generated during the muscular contraction are transmitted to the measuring devices without a delay moment or other sources of losses. Current stimulus intensities or the intensity of the impulse of the reflex hammer and the magnitude of the counterforce exerted on the investigated muscle by means of the device can be fixed exactly and in such a way that they cannot be changed during the investigation. The achieved measurement results, particularly for the total nerve potential, nerve conductive speed, total muscular potential, muscular force, muscular path, muscle vibration and the various latency periods are all quantified, determinable together, and can accordingly be correlated. In contrast to the known devices and methods, the device makes it possible to proportion the counterforce exerted by it on the muscle and to keep it constant along the area of movement during the contraction of the muscle. This is particularly important for recording the accompanying jerks characterizing the muscle and the Hill's equation between force and speed.

I claim:

1. A device for determining a change in mechanical magnitudes during muscular contraction and for correlating with a change in electrical magnitudes of nerve and muscle during muscular contraction in a body part having a joint with an axis of rotation, comprising:

a housing and within the housing, a member for supporting the body part;

two axles extending outward from said member and being supported for rotation in said housing so as to align horizontally with the axis of rotation of the joint;

means for exciting the muscle so that the muscle becomes contracted during a period of muscle contraction and thereby moves the body part rotatably about the axis of rotation of the axle joint to effect rotating movement, whereby said axles (7, 8) rotate in response to the rotating movement of the body part;

counterforce means coupled to one of said axles for providing a counterforce against the force of the muscle during the period of muscle contraction as caused by said exciting means; and measuring means for measuring muscular contraction and transmitting measured values indicative of said muscular contraction including potentiometer means attached to the other axle to measure angular positions of said axle in relation to the rotating movement of the body part during said period of muscle contraction; means for measuring a total nerve potential and conductive speed of the nerve including a first pair of electrodes (49, 50) attachable to the body part above a nerve of the contracted muscle; means for measuring electric potential fluctuations and including a second pair of electrodes (51, 52) attachable to the body part above the contracted muscle; means for measuring muscular vibration and including a stethoscope head (3) and microphone (54) coupled to the stethoscope head (3), said stethoscope head (3) being attachable to the body part above the contracted muscle; and means for simultaneously recording measured values delivered by said potentiometer means, said first and second pairs of electrodes and said microphone.

2. Device according to claim 1, wherein said housing (1) is formed with outer walls (12, 13);

said member for supporting the body part being in the form of a sagittally rotatable bolster (2); and said axles (7, 8) extending outward from said bolster (2) and passing through said outer walls (12, 13), said axles (7, 8) being formed to align horizontally with the axis of rotation of the joint.

3. Device according to claim 2, characterized in that a vertically arranged spiral spring (58) is attached to the outside of an outer wall (12), one end of the spiral spring (58) cooperating with a helical roller (57) attached on one of said axles (7) by means of a connection of material which is stable with respect to length, and its opposite end is attached to a flexure beam (59) attached at the outer wall (12), wherein the flexure beam is connected with an amplifier (40) and the means for recording (41).

4. Device according to claim 2, wherein said rotatable bolster has a U-shaped configuration defining a base portion and two vertical legs; and further comprising;
  a base plate (3) formed to accommodate the body part to be moved by means of the contracting muscle, said base plate (3) being attached on said base portion of said rotatable bolster (2); and
  means for vertically adjusting the body part, said vertically adjusting means including rotational adjustment means (14) for adjusting said base plate relative to said rotatable bolster so as to change relative inclination of said base plate (3) and thereby vertically adjust the body part accommodated thereon, said rotational adjustment means including a spherical head.

5. Device according to claim 4, characterized in that a support (16) is provided below a base plate (3) as a lower stop for the base plate (3), which support (16) is attached in a recess (17) in the outer wall (13) of the housing (1) so as to be fixed, but detachable and vertically adjustable, the recess (17) extending in a curve-shaped manner.

6. Device according to claim 4, characterized in that the rotational adjustment means (14) includes three pairs of corresponding disks (32), (33), (34), said pairs of disks being securely connected with respect to each other and detachable again and being arranged vertically one above the other and being connected with one another by means of one of the disks in each instance, a first and a second pair of said disks (32) (34) being arranged in a vertical direction so as to be offset by 90° relative to one another, and a third pair of said disks being arranged horizontally; and further comprising:
  scales (35), (36), (37) being arranged at each of said three pairs of disks.

7. Device according to claim 4, further comprising: a heel holder (6), which is displaceable in the longitudinal direction of the base plate (3) along a detachable fixing device in order to fix the body part placed on it, is attached at a rear end of the base plate (3).

8. Device according to claim 4, characterized in that feelers (38) for the adjustment of the base plate (3) to the anatomical shapes of the respective body part to be investigated via the rotational adjustment (14) are attached at the respective inner ends of the axles (7) and (8), which ends penetrate a vertical leg of the rotatable bolster (2), which feelers (38) can be pulled out of the axles in a telescopic manner or pressed in the axles by means of inserted springs.

9. Device according to claim 2, wherein said means for exciting the muscle includes an electric current source (23), said counterforce means including an electric coupling (10) having discs (18, 19) adjoining each other, at least one of said discs (18, 19) having a friction brake lining (20), said coupling being formed to respond to electromagnetic means (21, 22), said counterforce means further including an electric motor (9) connected to said electric coupling (10), both said electric motor (9) and said electric coupling (10) being connected to one of said axles (7) on one of said outer walls (12) of said housing (1) and being fed in a controllable manner by said electric current source (23).

10. Device according to claim 9, wherein said means for exciting the muscle includes an electric current stimulator and electrodes (42) attachable to places on the body part relevant for muscular excitation and being responsive to said current stimulator (39) and to said electric current source (23) for exciting the muscle; and further comprising;
  an amplifier (40) connected to all of said electrodes (49, 59, 51, 52), said microphone (54), said potentiometer means (11) and said electric motor (9), said amplifier being formed to amplify and transmit said measured values as amplified measured values; and
  recording means responsive to said amplifier for receiving and recording said amplified measured values.

11. Device according to claim 9, characterized in that the electric motor (9) has no rigid connection with the housing (26), and said at least one axle (7) is supported in an outer wall of the housing (26) in a ball bearing; and in that horizontally extending flexure beams (27), (28) are fastened to the housing (26) with stress measurement strips (29), (30) at both longitudinal sides of the electric motor (9).

12. Device according to claim 9, characterized in that a torque measuring strip (31) is attached to the other axle (8).

13. Device according to claim 4, characterized in that the base plate (3) comprises rotational adjustment means (14') with spherical head, wherein one or more measuring rods (55), which comprise resilient sleeves (56), are provided with scales and extend perpendicularly relative to the base plate (3), are attached at the underside of the base plate (3) and extend until a base piece of the rotating bolster (2).

14. Device according to claim 1, wherein said means for exciting the muscle includes an electric current source (23), a current stimulator (39) and additional electrodes (42) attachable to places on the body part relevant for muscular excitation and being responsive to said current stimulator (39) and to said electric current source (23) for exciting the muscle.

15. Device according to claim 14, further comprising;
  an amplifier (40) connected to all of said electrodes (49, 50, 51, 52), said microphone (54) and said potentiometer means (11), said amplifier being formed to amplify and to transmit said measured values as amplified measured values; and
  said recording means being responsive to said amplifier for receiving and recording said amplified measured values.

16. Device according to claim 15, wherein said additional electrodes are formed as surface electrodes.

17. Device according to claim 15, characterized in that said additional electrodes are formed as needle electrodes (43).

18. Device according to claim 1, further comprising: a limb holder (5) for the body part to be fixed is attached on the base plate (3) and consists of a cup of thermoflexible plastic in order to adapt to the shape of the respective body part.

19. Device according to claim 1, characterized in that said means for exciting the muscle includes a reflex hammer (44) with a hammer head (47) and includes a piezoelectric element (48) in said hammer head (77), said piezoelectric element (48) being formed to transmit an electric impulse to a tendon or muscle when said hammer (44) strikes the tendon or muscle; and further comprising:
  means for triggering said reflex hammer, said triggering means including spring means (45) and a catch (46), said spring means (45) biasing against said hammer head (47) and being formed to tension and relax in response to said catch (46) so as to trigger said reflex hammer.

20. Device according to claim 1 and further comprising:
- a rear wall (24) of said housing;
- an upper limb holder (4);
- adjusting screw means for vertically and horizontally adapting said upper limb holder to the body part to be investigated; and
- binding means for fixing said upper limb holder to the body part to be investigated; said binding means being attached at the rear wall (24) of said housing.

21. Device according to claim 1, further comprising: a housing (1) with a wall (12), one of said axles (7) extending outward from said wall (12), said counterforce means including a toothed rail (61) with one end, a toothed gear (60) meshing with said toothed rail (61) piston (63) at said one end of said toothed rail (61), a compressed air tank (65) with an output (64) into which is inserted said piston (63), said piston (63) being formed so as to be displaceable in said output at said axle (7) outside of said wall (12) of said housing (1) via said toothed gear (60) and said toothed rail (61).

22. Device according to patent claim 1, characterized in that, a U-shaped structural component part (72), with the axles (68) attached to its two opposite ends, and a strip (73) attached to the structural component part (72) by means of a fixing joint (74), is fastened to the body part to be investigated, wherein the axles (68) lie on a horizontal, imaginary line with the axles of rotation of the joint of the body part to be investigated and are supported at the end points of another U-shaped structural component part (69), which is fastened to an inherently rigid holder (70) for the body part to be investigaged by means of a adjusting device (71), on which a measurement scale is attached and which can be pulled out and can be rotated in a three-dimensional manner.

23. A device for determining a change in mechanical magnitudes during muscular contraction and for correlating with a change in electrical magnitudes of nerve and muscle during muscular contraction in a body part having a joint with an axis of rotation, comprising:
- a housing (11) with outer walls (12, 13);
- a sagittally rotatable bolster (2);
- means for supporting said bolster (2) in said housing (11), said supporting means including two axles (7, 8) extending outward from said rotatable bolster and leading through said outer walls (12, 13), said axles (7, 8) being formed to align horizontally with the axis of rotation of the joint;
- an electric current source (23);
- a current stimulator (39) connected to said electric current source (23);
- means for exciting the muscle, said exciting means including surface electrodes (42) attachable to places on the body part relevant for muscular excitation and being responsive to said current stimulator (39);
- an electric coupling (10) having discs (18, 19) adjoining each other, at least one of said discs (18, 19) having a friction brake lining (20), said coupling being formed to respond to electromagnetic means (21, 22);
- an electric motor (9) connected to said electric coupling (10), both said electric motor (9) and said electric coupling (10) being connected to one of said axles (7) on said outer wall (12) of said housing (1) and being red in a controllable manner by said electric current source (23);
- first means for measuring muscular contraction, said first measuring means being formed to transmit measured values indicative of said muscular contraction and including a potentiometer means (11) attached to the other axle (8) at an outside of said outer wall (13) of said housing (1), second means for measuring a total nerve potential and for measuring a conductive speed of the nerve, said second measuring means including electrodes (49, 50) attachable above the nerve of the contracted muscle, and third means for measuring electric potential fluctuations, said third measuring means including electrodes (51, 52) attachable above the contracted muscle, a stethoscope head (53) attachable above the contracted muscle, and a microphone (54) coupled to the stethoscope head (53);
- an amplifier (40) connected to the electrodes (49, 50, 51, 52) of the second and third measuring means and the microphone (54) of the stethoscope head (53) and the potentiometer means (11) and the electric motor (9), said amplifier being formed to amplify said measured values so as to form and transmit amplified measured values; and
- recording means for recording the amplified measured values, said recording means being connected to said amplifier for receiving and recording said amplified measured values.

24. A device for determining a change in mechanical and/or electrical magnitudes during muscular contraction and for correlating with a change in electrical magnitudes of nerve and muscle during muscular contraction in a body part having a joint with an axis of rotation, comprising:
- a stationary member;
- a supporting member for supporting the body part;
- axles extending outward from the supporting member and being mounted for rotation on the stationary member;
- means for fixing the body part on the stationary and supporting members;
- means for adjusting the position of the body part on the supporting member so as to align the axis of rotation of the joint with the axles;
- means for exciting the muscle so that the muscle becomes contracted during a period of muscle contraction and thereby moves the body part rotatably about the axis of rotation of the joint to effect rotating movement, whereby the supporting member and the axles rotate in response to the rotating movement of the body part;
- counterforce means for providing a counterforce against the force of the muscle during the period of muscle contraction as caused by said excitation means;
- means for measuring one or more of the rotation of the axles during the muscular contraction, electrical signals generated during the muscular contraction, and electrical magnitude of the nerve during the muscular contraction, the measuring means being formed to transmit values indicative of the muscular contraction; and
- means for receiving the measured values and recording the same.

25. Device according to claim 24, characterized in that, said counterforce means includes a the frame construction (80, 81, 82) attached at one of said axles (7, 68) at an outer side (12) of a housing (1), and inner struts (83), which extend parallel to outer struts (82) through recesses in a base plate (80) and a cover plate of the frame construction (81) and are securely connected by means of a center plate (78), are displaceable in the frame construction (80, 81, 82); and in that the center plate (78) cooperates with a lever (75) by means of a movable double roller (77) lying on top of it, wherein the lever (75) is connected with said one of said axles (7, 68) at a right angle via a guide (76) and so as to be displaceable in the guide (76), and the lever (75) is guided at its opposite end in two elongated holes (87) of side walls (84) of the frame construction (80, 81, 82) in the area of the double roller (77) via axial elongations (86), the side walls (84) being located opposite one another; the two elongated holes (87) describing a mathematically determined curve; and in that a compressible pressure spring (79) is tensioned between the base plate (80) and the center plate (78).

26. Device according to claim 25, characterized in that a lower end of the pressure spring (79) is inserted in an area of the base plate (80) in a cup-shaped supporting cylinder (85), which is detachably attached to the base plate (80) by means of a bayonet lock, known per se, the pressure spring (79) extending through a corresponding opening of the base plate (80) until the center plate (78), and pressure springs having different spring constants can be used interchangeably.

27. Device according to claim 25, characterized in that stress measurement strips (88) are attached to the lever (75).

28. Device according to claim 24 for the investigation of muscular contraction in smaller joints and muscles, characterized in that the body part to be investigated, with its portion which is moved by means of the contraction of the muscle, e.g. the thumb, is placed in a cup 94 and fastened in the latter, while the portion of the body part which is not moved, e.g. the rest of the hand, is inserted and fixed in a holder 97, 98, 99, 100, wherein the holder consists of a base 97, a rigid outer wall 98, which is attached to the latter at a right angle, and outer walls 99, 100, which are displaceable in a direction of the outer wall 98 by means of lockable rail guides 101 and 102 and are likewise arranged at a right angle to the base 97 is adapted to the shape and attitude of the body part by means of the outer walls 99, 100 and a support bar 105, which is fastened on the base plate 106 by means of the graduated and fixable ball joint 104, 104' and is likewise graduated and longitudinally displaceable within the ball joint 103, 103', and which is arranged so as to be attached at the base 97 and with graduated and fixable ball joint 103, 103' and, further, in that the cup 94 is securely connected with a known fastening joint via a holder 95 and with the axle 90 via a stirrup 93, and there are measuring rods 96 at the two ends of the stirrup 93 for fixing the joint of the investigated body part on the imaginary line of the axis of articulation with one of said axles 90; in that a translating gear wheel 113, which comprises a thread arranged on its circumference, and, following this, the potentiometer 11 for measuring the force of the rotational movement during the rotation of the axle 90, are attached on said one of said axles 90 at the longitudinal side opposite the stirrup 93; further, in that the translating gear wheel 113 cooperates with the rod 117, which is arranged at a right angle to said one of said axles 90, but is not connected with the latter or with the translating gear wheel 113 so as to be fixed, which rod 117 is movable in its longitudinal direction in linear guides 118; 119, 120 and comprises two cord/wire holders 115, 116 with a pretensioning device at least one of the holders in the area assigned to the translating gear wheel; both ends of the cord/wire 114 inserted in the thread of the translating gear wheel 113 being fastened in the holders; further, in that the rod 117 has an electric winding 123 with a coil holder 122 at its end downstream of the linear guide 119, 120, the electric winding 123 penetrating a magnet core 124, which is attached separately at the base plate 106, and being fed in a controllable manner by means of an electric current source 23 and the current regulator 121 and being pulled in or pressed out of the magnet core 124 with the rod 117 according to the intensity of the magnetic field; moreover, in that the force which acts on the rod 117, is generated by the contracting muscle, and is transmitted via the stirrup 93, said one of said axles 90 and the translating gear wheel 113, as well as the determined counterforce exerted by the solenoid coil 122, 123, 124, are recorded by means of a tension/-compression recorder 126, wherein the recorded data is amplified in the amplifier 40, and is recorded in the recording device 41; and in that the lock 125 is provided for the secure adjustment of the rod 117 in predetermined positions of its longitudinal direction, preferably as a coil/magnet core switch, which is likewise controllable via the current regulator 121; and in that said one of said axles 90 is supported in two ball bearings 91 arranged within the bearing support pipe 92, and the bearing support pipe 92 is in turn rigidly connected with the housing wall 108 which extends vertically relative to the base plate 106.

29. A device according to claim 24 wherein said measuring means include electrodes attachable above a nerve of the body part to measure a nerve potential and/or the conductive speed of the nerve, electrodes attachable above or in the muscle to measure electric potential fluctuations thereof, a microphone attachable above the muscle to measure vibrations thereof, means for measuring the contraction force of the muscle, and a potentiometer attached to at least one of the axles to measure the mechanical magnitude and/or the velocity of the muscle contraction.

* * * * *